US010526357B2

(12) United States Patent
Shorr et al.

(10) Patent No.: US 10,526,357 B2
(45) Date of Patent: *Jan. 7, 2020

(54) PHARMACEUTICAL COMPOUNDS

(71) Applicant: Rafael Pharmaceuticals, Inc., Cranbury, NJ (US)

(72) Inventors: Robert Shorr, Edison, NJ (US); Robert Rodriguez, West Windsor, NJ (US); Paul Bingham, Centereach, NY (US); Lakmal Boteju, Kendall Park, NJ (US); Thomas Kwok, Miller Place, NY (US); James Marecek, Saint James, NY (US)

(73) Assignee: Rafael Pharmaceuticals, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/212,746

(22) Filed: Dec. 7, 2018

(65) Prior Publication Data
US 2019/0119309 A1 Apr. 25, 2019

Related U.S. Application Data

(63) Continuation of application No. 15/487,980, filed on Apr. 14, 2017, now Pat. No. 10,179,796, which is a continuation of application No. PCT/US2014/000150, filed on Jun. 19, 2014.

(51) Int. Cl.
| | |
|---|---|
| *C07D 257/04* | (2006.01) |
| *C07F 9/54* | (2006.01) |
| *C07C 323/12* | (2006.01) |
| *C07C 323/66* | (2006.01) |
| *C07C 321/20* | (2006.01) |
| *C07C 323/25* | (2006.01) |
| *C07C 323/60* | (2006.01) |

(52) U.S. Cl.
CPC .......... *C07F 9/5442* (2013.01); *C07C 321/20* (2013.01); *C07C 323/12* (2013.01); *C07C 323/25* (2013.01); *C07C 323/60* (2013.01); *C07C 323/66* (2013.01); *C07D 257/04* (2013.01)

(58) Field of Classification Search
None
See application file for complete search history.

(56) References Cited

U.S. PATENT DOCUMENTS

| | | | |
|---|---|---|---|
| 2,805,251 A | 9/1957 | Marshall et al. | |
| 2,809,978 A | 10/1957 | Holly et al. | |
| 2,852,531 A | 9/1958 | Hoffman et al. | |
| 2,875,238 A | 2/1959 | Holly et al. | |
| 2,875,239 A | 2/1959 | Holly et al. | |
| 2,975,198 A | 3/1961 | Reed | |
| 2,980,716 A | 4/1961 | Reed | |
| 2,985,685 A | 5/1961 | Thomas et al. | |
| 3,002,011 A | 9/1961 | Holly et al. | |
| 3,345,368 A | 10/1967 | Lewis et al. | |
| 3,453,312 A | 7/1969 | Sprague | |
| 3,881,017 A | 4/1975 | Vlattas | |
| 3,970,670 A | 7/1976 | Vlattas | |
| 4,041,047 A | 8/1977 | Vlattas | |
| 4,077,979 A | 3/1978 | Vlattas | |
| 4,077,980 A | 3/1978 | Vlattas | |
| 4,705,867 A | 11/1987 | Giray et al. | |
| 4,800,044 A | 1/1989 | Giray et al. | |
| 4,966,732 A | 10/1990 | Giray et al. | |
| 5,344,941 A | 9/1994 | Samour et al. | |
| 5,463,093 A | 10/1995 | Garnett | |
| 5,508,275 A | 4/1996 | Weithmann et al. | |
| 5,569,670 A | 10/1996 | Weischer et al. | |
| 5,679,697 A | 10/1997 | Garnett | |
| 5,750,141 A | 5/1998 | Roberts et al. | |
| 6,117,902 A | 9/2000 | Quash et al. | |
| 6,331,559 B1 | 12/2001 | Bingham et al. | |
| 6,605,637 B1 | 8/2003 | Harnett et al. | |
| 6,951,887 B2 | 10/2005 | Bingham et al. | |
| 7,220,428 B2 | 5/2007 | Shorr et al. | |
| 7,232,919 B2 | 6/2007 | Lal | |
| 7,387,790 B2 | 6/2008 | Shorr et al. | |
| 7,521,066 B2 | 4/2009 | Shorr et al. | |
| RE43,295 E | 4/2012 | Shorr et al. | |
| 8,263,653 B2 | 9/2012 | Shorr et al. | |

(Continued)

FOREIGN PATENT DOCUMENTS

| | | |
|---|---|---|
| GB | 758897 A | 10/1956 |
| JP | 2007/077066 A | 3/2007 |

(Continued)

OTHER PUBLICATIONS

PubChem SureCN10307812, CID 59419964, Create Date: Aug. 20, 2012, IUPAC Name: 1-benzylsulfanyloctan-3-ylsulfanylmethylbenzene. Retrieved from the Internet at http://pubchem.ncbi.nlm.nih.gov/compound/59419964. (12 pages).

Crévisy et al. (1998) "A New Iron-Mediated Strategy for the Synthesis of α-Lipoic Acid and Analogues" *Eur. J. Org. Chem.* pp. 1949-1954.

Handbook of Pharmaceutical Salts: Properties, Selection and Use, IUPAC, Wiley-VCH, P.H. Stahl ed., p. 342.

Benson "Transdermal Drug Delivery: Penetration Enhancement Techniques," *Current Drug Delivery*, vol. 2, No. 1, pp. 23-33 (2005).

(Continued)

*Primary Examiner* — Alicia L Otton

(74) *Attorney, Agent, or Firm* — Dechert LLP

(57) ABSTRACT

Therapeutically-effective amounts of novel analogs or derivatives of alkyl fatty acids, such as but not limited to lipoic acid, and pharmaceutical formulations comprising such analogs or derivatives and pharmaceutically-acceptable carriers therefor, are useful for the treatment, prevention, imaging, and/or diagnosis of medical disorders.

18 Claims, No Drawings

(56) References Cited

U.S. PATENT DOCUMENTS

| | | | |
|---|---|---|---|
| 8,691,873 | B2 | 4/2014 | Shorr et al. |
| 8,785,475 | B2 | 7/2014 | Bingham et al. |
| 9,150,509 | B2 | 10/2015 | Bingham et al. |
| 9,320,726 | B2 | 4/2016 | Shorr et al. |
| 9,839,691 | B2 | 12/2017 | Shorr et al. |
| 9,872,845 | B2 | 1/2018 | Shorr et al. |
| 10,098,955 | B2 | 10/2018 | Shorr et al. |
| 10,179,796 | B2 | 1/2019 | Shorr et al. |
| 2005/0048008 | A1 | 3/2005 | Gupta |
| 2008/0262034 | A1 | 10/2008 | Bingham et al. |
| 2008/0262077 | A1* | 10/2008 | Shorr .................. A61K 31/19 514/440 |
| 2009/0036356 | A1 | 2/2009 | Patell et al. |
| 2010/0190858 | A1 | 7/2010 | Shorr et al. |
| 2011/0212954 | A1 | 9/2011 | Brufani et al. |
| 2012/0178812 | A1 | 7/2012 | Shorr et al. |
| 2013/0150445 | A1 | 6/2013 | Shorr et al. |
| 2014/0364502 | A1 | 12/2014 | Bingham et al. |
| 2015/0011633 | A1 | 1/2015 | Shorr et al. |
| 2015/0322103 | A1 | 11/2015 | Shorr et al. |
| 2016/0220678 | A1 | 8/2016 | Shorr et al. |
| 2017/0056355 | A1 | 3/2017 | Shorr et al. |
| 2017/0217998 | A1 | 8/2017 | Shorr et al. |
| 2017/0218003 | A1 | 8/2017 | Shorr et al. |
| 2018/0273551 | A1 | 9/2018 | Shorr et al. |
| 2019/0015512 | A1 | 1/2019 | Shorr et al. |

FOREIGN PATENT DOCUMENTS

| | | |
|---|---|---|
| JP | 4728481 B2 | 7/2011 |
| WO | WO-2000/024734 A1 | 5/2000 |
| WO | WO-2008/131114 A2 | 10/2008 |
| WO | WO-2008/131117 A1 | 10/2008 |
| WO | WO-2009/110859 A1 | 9/2009 |
| WO | WO-2009/123597 A1 | 10/2009 |
| WO | WO-2010/019225 A1 | 2/2010 |
| WO | WO-2010/062381 A1 | 6/2010 |
| WO | WO-2010/110771 A2 | 9/2010 |
| WO | WO-2010/110887 A1 | 9/2010 |
| WO | WO-2011/005310 A1 | 1/2011 |
| WO | WO-2011/005311 A1 | 1/2011 |
| WO | WO-2011/046583 A1 | 4/2011 |
| WO | WO-2011/050261 A1 | 4/2011 |
| WO | WO-2011/143590 A1 | 11/2011 |
| WO | WO-2011/143593 A1 | 11/2011 |
| WO | WO-2014/098926 A1 | 6/2014 |
| WO | WO-2016/065360 A1 | 4/2016 |

OTHER PUBLICATIONS

International Search Report for International Application No. PCT/US2008/060650 dated Jul. 18, 2008 (1 page).
Nakano et al. (1955) "Studies on α-Lipoic Acid and its Related Compounds. I. Synthesis of DL-α-Lipoic Acid" *Yakugaku Zasshi*, 75(10):1296-1298. (with English abstract).
Nakano (1956) "Studies on α-Lipoic Acid and its Related Compounds. IV. On Acetylation of Ethyl DL-Dihydro-α-lipoate" *Yakugaku Zasshi*, 76(10):1207-1209. (with English abstract).
Pan et al. (1998) "D,L-S-Methyllipoic Acid Methyl Ester, a Kinetically Viable Model for S-protonated Lipoic Acid as the Oxidizing Agent in Reductive Acyl Transfers Catalyzed by the 2-Oxoacid Dehydrogenase Multienzyme Complexes" *Biochemistry* 37(5):1357-1364.
Schoberl et al. (1958) *Justus Liebigs Ann. Chem.* 614:66-83. (with English translation).
Soper et al. (1954) "Syntheses of DL-α-Lipoic Acid" *J. Am. Chem. Soc.* 76:4109-12.
Supplementary European Search Report and Search Opinion dated May 19, 2010 in European Patent Application No. 08780538 (7 pages).
Thomas et al. (1955) "Synthesis and Properties of High Specific Activity DL-α-Lipoic Acid-$S_2^{35}$" *J. Am. Chem. Soc.* 77(20):5446-5448.
Thomas et al. (1956) "Synthesis of DL-1,2-Dithiolane-3-Caproic Acid and DL-1,2-Dithiolane-3-Butyric Acid, Homologs of α-Lipoic Acid" *J. Am. Chem. Soc.* 78(23):6151-6153.
T. Higuchi and K. Kato, J. Pharm. Sci. (1966) vol. 55, pp. 1080-1084.
T. Higuchi et al., Anal. Chem. (1967) vol. 39, pp. 974-979.
A.F. Michaelis and T. Higuchi, in J. Pharm. Sci. (1969) vol. 58, pp. 201-204.
Daigo et al. (1962) "Synthesis of Some N-Lipoyl Amino Acids and Peptides" J. Am. Chem. Soc. 84(4):662-665.
Kieler et al. (1967) "The Effect of Structural Analogues of α-lipoic Acid on the Growth and Metabolism of L-Fibroblasts and Ehrlich Cells" Archivum Immunologiae et Therapiae Experimentalis, vol. 15, pp. 106-108.
Rastetter et al. (1981) "α-Keto Acid Dehydrogenases: A Chemical Model" J. Org. Chem. 46(9):1882-1887.
Reed et al. (1955) "Synthesis of DL-α-Lipoic Acid" J. Amer. Chem. Soc. 77:416-419.
Shih et al. (1974) "Properties of Lipoic Acid Analogs" J. Heterocycl. Chem. 11:119-123.
Watabe et al. (2007) "ATP depletion does not account for apoptosis induced by inhibition of mitochondrial electron transport chain in human dopaminergic cells" Neuropharmacology 52(2):536-541.
English Translation of Nakano et al. in Yakugaku Zasshi (1956), 76, 943-7.
Automated CellTiter-Glo® Luminescent Cell Viability Assay Protocol, Promega, Part # EP014, (2009).
Search Report from European Patent Application No. 08780538.8 dated Feb. 24, 2012 (5 pages).
Serajuddin (2007) "Salt formation to improve drug solubility" ScienceDirect, Advanced Drug Delivery Reviews, vol. 59, pp. 603-616.
Zong et al. (2006) "Necrotic death as a cell fate" Genes & Development, vol. 20, pp. 1-15.
Stott et al.(2004) "Evaluation of the Potential of Triethanolamine to Alter Hepatic Choline Levels in Female B6C3F1 Mice" *Toxicological Sciences*, vol. 79, pp. 242-247.
Johar D. et al. (2004) "Inflammatory response, reactive oxygen species, programmed (necrotic-like and apoptotic) cell death and cancer" *Roczniki Akademni Medycznej w Bialymstoku*, vol. 49, Annales Academiae Medicae Bialostocensis, pp. 31-39.
International Search Report and Written Opinion for International Application No. PCT/US2010/053728 dated Mar. 24, 2011 (9 pages).
Adams (1955) "Thioctic-S352 Acid: Synthesis and Radiation Decomposition" JACS 77:5357-5359.
International Preliminary Report on Patentability for International Application No. PCT/US2008/060650 dated Dec. 7, 2009, (6 pages).
Bastin et al. "Salt Selection and Optimisation Procedures for Pharmaceutical New Chemical Entities," Organic Process Research & Development, 2000, vol. 4, pp. 427-435.
Patani et al. (1996) "Bioisosterism: A Rational Approach in Drug Design" *Chem. Rev.*, 96:3147-3176.
Thiesen et al., "Physico-chemical stability of docetaxel premix solution and docetaxel infusion solutions in PVC bags and polyolefine containers" (1999), *Pharm, World Sci.*, 21(3), pp. 137-141.
Ames Laboratory. "What are the Rare Earths?" Downloaded on Nov. 4, 2016 from https://www.ameslab.gov/dmse/rem/what-are-rare-earths.
Rare Element Resources. "Rare Earth Elements" Downloaded on Nov. 4, 2016 from http://www.rareelementresources.com/rare-earth-elements#.WBz84PIVgVs.
Stoffregen, S. A. et al. "Thioether Complexes of Palladium(II) and Platinum(II) as Artificial Peptidases. Residue-Selective Peptide Cleavage by a Palladium(II) Complex," *Inorg. Chem.* (2005) vol. 44, pp. 8899-8907.
Berge S. et al. (1977) "Pharmaceutical Salts," Journal of Pharmaceutical Sciences, 66(1): 1-19.
Bullock et al., Syntheses in the Thioctic Acid Series, 76 J. Am. Chem. Soc. 1828-32 (1954).
D. Feller, et al., "Selective PPARgamma versus PPARalpha agonist activity of a novel set of alpha-lipoic acid analogs of thiazolidinediones,"

(56) References Cited

OTHER PUBLICATIONS

FASEB Journal, vol. 17, No. 4-5 (Mar. 2003), XP009133351; FASEB Meeting Experimental Biology, Translating the Genome, San Diego, CA (Apr. 2003).
Kintzel et al. "Practical guidelines for preparing and administering amphotericin B", 1992, *Am. J. Hosp. Pharm.*, 49(5): 1156-64, Pub Med abstract, PMID: 1595747.
National Toxicology Program (NTP) (1999). Toxicology and Carcinogenesis Studies of Triethanolamine (CAS No. 102-71-6) in F344/N Rats and B6C3F1 Mice (Dermal Studies), NTP TR 449, NIH Publication No. 00-3365.
National Toxicology Program (NTP), "Toxicology and Carcinogenesis Studies of Triethanolamine (CAS No. 102-71-6) in B6C3F1 Mice (Dermal Study)", NTP TR 518, NIH Publication No. 04-4452., (2004).
Richard B. Silverman, The Organic Chemistry of Drug Design and Drug Action, Chapter 2: Drug Discovery, Design, and Development, Academic Press, p. 5-51 (1992).
S. Satoh, et al., "Simultaneous determination of alpha-lipoic acid and its reduced form by high-performance liquid chromatography with fluorescence detection," Journal of Chromatography B, 854, pp. 109-115 (2007).
Supplementary European Search Report for European Application No. 08754909.3, dated May 19, 2010, 11 pages.
Surya Kanta De, "Yttrium Triflate as an Efficient and Useful Catalyst for Chemoselective Protection of Carbonyl Compounds," Tetrahedron Letters, vol. 45, pp. 2339-2341 (2004).
W. Hyk, et al., "The extreme migrational enhancement of faradaic current at microelectrodes: experimental studies on sodium (6,8-diferrocenylmethylthio)octanoate electrooxidation," Journal of Electroanalytical Chemistry 575, pp. 321-328 (2005).
Written Opinion for International Application No. PCT/US08/60655, dated Jul. 17, 2008, 4 pages.
Kono, Y. et al. "Antiproliferative effects of a new α-lipoic acid derivative, DHL-HisZnNa, in HT29 human colon cancer cells in vitro," *Expert Opinion on Therapeutic Targets* (2012), vol. 16, pp. S103-S109.
https://clinicaltrials.gov/ct2/results?term=cpi-613&Search=Search, accessed Apr. 8, 2015.
https://clinicaltrials.gov/ct2/show/NCT01832857?term=cpi-613+colon&rank=2, accessed Apr. 8, 2015.
https://clinicaltrials.gov/ct2/show/NCT01766219?term=cpi-613+liver&rank=1, accessed Apr. 8, 2015.
International Search Report and Written Opinion for International Application No. PCT/US2014/000150 dated Oct. 7, 2014 (7 pages).
International Search Report and Written Opinion for International Application No. PCT/US2014/000149 dated Oct. 23, 2014 (5 pages).
Beuerle, T. et al. "Isolation, Identification, and Enantioselective Synthesis of Octane-1,3,7-triol: Determination of Its Absolute Configuration," J. Nat. Prod. (1999), vol. 62, No. 1, pp. 35-40.
Bose, D. S. et al. "An Efficient, Highly Enantioenriched Route to L-Carnitine and a-Lipoic Acid via Hydrolytic Kinetic Resolution," Synthesis (2006), No. 11, pp. 1863-1867.
Brown, S. et al. "Targeting lipoic acid to mitochondria: Synthesis and characterization of a triphenylphosphonium-conjugated a-lipoyl derivative," Free Radical Biology & Medicine (2007), vol. 42, No. 12, pp. 1766-1780.
Chandrasekhar, S. et al. "Spirastrellolide B: The Synthesis of Southern ($C_9$-$C_{25}$) Region," Organic Letters (2008), vol. 10, No. 19, pp. 4355-4357.
Li, P. et al. "Stereoselective Total Synthesis of Etnangien and Etnangien Methyl Ester," J. Org. Chem. (2010), vol. 75, No. 8, pp. 2429-2444.
Reddy, N. K. and Chandrasekhar, S. "Total Synthesis of (-)-a-Kainic acid via Chirality Transfer through Ireland-Claisen Rearrangement," J. Org. Chem. (2013), vol. 78, No. 7, pp. 3355-3360.
Yadav, J. S. et al. "Single step transformation of PMB ethers to bromides using a $CBr_4$-TPP reagent system," Tetrahedron Letters (2002), vol. 43, No. 31, pp. 5419-5422.
CAS Registry No. 1246510-62-2; CAS Registry Database; STN Entry Date: Oct. 19, 2010; Chemical name: 2H-Tetrazole, 2-[5,7-bis[(phenylmethyl)thio]heptyl]-.
U.S. Appl. No. 16/039,799, Pharmaceutical Formulations Containing Lipoic Acid Derivatives, filed Jul. 19, 2018.
U.S. Appl. No. 15/898,709, Pharmaceutical Compounds, filed Feb. 19, 2018.
U.S. Appl. No. 15/487,970, Pharmaceutical Compounds, filed Apr. 14, 2017.

\* cited by examiner

PHARMACEUTICAL COMPOUNDS

CROSS REFERENCE TO RELATED APPLICATIONS

This application is a continuation of U.S. patent application Ser. No. 15/487,980, filed Apr. 14, 2017, which is a continuation of International (PCT) Patent Application Serial No. PCT/US2014/000150, filed Jun. 19, 2014; the contents of each of which are hereby incorporated by reference in their entirety.

FIELD OF THE INVENTION

This invention relates to pharmaceutical agents, and more particularly to therapeutic agents comprising novel analogs and derivatives of alkyl fatty acids, such as but not limited to lipoic acid, and pharmaceutically-acceptable formulations and methods of use therefor.

BACKGROUND OF THE INVENTION

The precise mechanism by which cancer arises continues to be the subject of intense investigation, and thus a unifying theory of the origin of cancer remains elusive. Recent research has confirmed that cancer is a disease arising from a patient's own cells and tissue. Indeed, it is now known that an individual patient may possess multiple tumor cell types, which may not be the same across patients with the same diagnosis or even in the same patient (with disease progression being a further compounding factor). In any event, the highly individualized nature of the disease is an important factor in driving the need for personalized medicine. That 1.2 million Americans are newly diagnosed each year with cancer; that 10 million Americans are living with the disease; and that cancer may become the leading cause of disease-related death makes the establishment of new treatment approaches especially urgent.

It has been observed that the vast majority of fast-growth tumor cells exhibits profound genetic, biochemical, and histological differences with respect to nontransformed cells, including a markedly-modified energy metabolism in comparison to the tissue of origin. The most notorious and well-known energy metabolism alteration in tumor cells is an increased glycolytic capacity even in the presence of a high $O_2$ concentration, a phenomenon known as the Warburg effect. Consequently, glycolysis generally believed to be the main energy pathway in solid tumors. There is also a direct correlation between tumor progression and the activities of the glycolytic enzymes hexokinase and phosphofructokinase (PFK) 1, which are greatly increased in fast-growth tumor cells. Accordingly, it has been postulated that tumor cells that exhibit deficiencies in their oxidative capacity are more malignant than those that have an active oxidative phosphorylation. No matter whether under hypoxic or aerobic conditions, then, cancer tissue's reliance on glycolysis is associated with increased malignancy.

The pyruvate dehydrogenase (PDH) complex has been associated with the Warburg effect. (See, e.g., McFate T, Mohyeldin A, Lu H, Thakar J, Henriques J, Halim N D, Wu H, Schell M J, Tsang T M, Teahan O, Zhou S, Califano J A, Jeoung N H, Harris R A, and Verma A (2008). Pyruvate dehydrogenase complex activity controls metabolic and malignant phenotype in cancer cells. *J Biol Chem* 283: 22700-8, herein incorporated by reference.) The transition to Warburg metabolism therefore requires shutting down the PDH complex. In this transition, there is enhanced signalling by hypoxia-inducing factor (HIF) in cancer cells, which in turn induces the overexpression of pyruvate dehydrogenase kinase (PDK) 1, which is particularly effective in maintaining an inactive PDH complex. However, alterations in PDK1 observed in cancer may not only be due to changes in its concentration but also to changes in its activity and possibly in its amino acid sequence, even between one tumor type or one patient to another. Additionally, PDK1 may form different complexes with various molecules associated with tumors depending upon the tumor type presented. Recent studies suggest that forcing cancer cells into more aerobic metabolism suppresses tumor growth. Furthermore, PDH complex activation may lead to the enhanced production of reactive oxygen and nitrogen species (RONS), which may in turn lead to apoptosis. Thus, inhibition of PDK may be a potential target in generating apoptosis in tumors. However, to date, known PDK1 inhibitors have been demonstrated to cause maximally only 60% inhibition of this isozyme.

While traditional chemotherapy targets dividing, proliferating cells, all clinically-accepted chemotherapeutic treatments use large drug doses that also induce profound damage to normal, proliferative host cells. On the other hand, drug delivery to a hypoxic region in solid tumors may be difficult when the drug does not permeate through the different cellular layers easily. Therefore, more selective targeting is required for the treatment of cancer. Another problem associated with chemotherapy is that, in many tumor types, there is either inherent or acquired resistance to antineoplastic drugs. Overall, traditional chemotherapy currently offers little long-term benefit for most malignant tumors and is often associated with adverse side-effects that diminish the length or quality of life.

Hence, radical new approaches are required that can provide long-term management of tumors while permitting a decent quality of life. To fulfill these imperatives, it would be advantageous to design anticancer agents having metabolic inhibition constants in at least the submicromolar range. Concentrating on the Warburg effect allows for designing drugs based on the physico- and biochemical energetic differences between tumor and normal cells to facilitate the design of delivery and therapeutic strategies that selectively affect solely tumor metabolism and growth without affecting healthy tissue function.

Lipoic acid (6,8-dithiooctanoic acid) is a sulfur-containing antioxidant with metal-chelating and anti-glycation capabilities. Lipoic acid is the oxidized part of a redox pair, capable of being reduced to dihydrolipoic acid (DHLA). Unlike many antioxidants that are active only in either the lipid or the aqueous phase, lipoic acid is active in both lipid and aqueous phases. The anti-glycation capacity of lipoic acid combined with its capacity for hydrophobic binding enables lipoic acid to prevent glycosylation of albumin in the bloodstream. Lipoic acid is readily absorbed from the diet and is rapidly converted to DHLA by NADH or NADPH in most tissues. Additionally, both lipoic acid and DHLA are antioxidants capable of modulating intracellular signal transduction pathways that use RONS as signalling molecules.

It is uncertain whether lipoic acid is produced by cells or is an essential nutrient, as differences in intracellular concentration may exist between tissue types as well as between healthy and diseased cells or even between individuals within a species. Mitochondrial pumps or uptake mechanisms, including binding and transport chaperones, may be important in transporting lipoic acid to mitochondria. It is already known that the expression levels and stoichiometry of the subunits comprising many of the lipoic acid-utilizing enzymes, which are linked to energy metabolism as well as growth, development and differentiation, vary with diet and exercise as well as genetics. The role of lipoic acid as a cofactor in the PDH complex of healthy cells has been well studied. The PDH complex has a central E2 (dihydrolipoyl transacetylase) subunit core surrounded by the E1 (pyruvate dehydrogenase) and E3 (dihydrolipoyl dehydrogenase) subunits to form the complex; the analogous alpha-ketoglutarate dehydrogenase (α-KDH), acetoin dehydrogenase (ADH), and branched chain alpha-keto acid dehydrogenase (BCK-ADH) complexes also use lipoic acid as a cofactor. In the gap between the E1 and E3 subunits, the lipoyl domain ferries intermediates between the active sites. The lipoyl domain itself is attached to the E2 core by a flexible linker. Upon formation of a hemithioacetal by the reaction of pyruvate and thiamine pyrophosphate, this anion attacks the S1 of an oxidized lipoate species that is attached to a lysine residue. Consequently, the lipoate S2 is displaced as a sulfide or sulfhydryl moiety, and subsequent collapse of the tetrahedral hemithioacetal ejects thiazole, releasing the TPP cofactor and generating a thioacetate on the S1 of the lipoate. At this point, the lipoate-thioester functionality is translocated into the E2 active site, where a transacylation reaction transfers the acetyl from the "swinging arm" of lipoate to the thiol of coenzyme A. This produces acetyl-CoA, which is released from the enzyme complex and subsequently enters the TCA cycle. The dihydrolipoate, still bound to a lysine residue of the complex, then migrates to the E3 active site, where it undergoes a flavin-mediated oxidation back to its lipoate resting state, producing $FADH_2$ (and ultimately NADH) and regenerating the lipoate back into a competent acyl acceptor.

U.S. Pat. Nos. 6,331,559 and 6,951,887 to Bingham et al., as well as U.S. patent application Ser. No. 12/105,096 by Bingham et al., all herein incorporated by reference, disclose a novel class of lipoic acid derivative therapeutic agents that selectively target and kill both tumor cells and certain other types of diseased cells through targeting disease-specific enzymes and multi-enzyme complexes. These patents further disclose pharmaceutical compositions, and methods of use thereof, comprising a therapeutically-effective amount of such lipoic acid derivatives along with a pharmaceutically-acceptable carrier therefor. The present inventors have now discovered additional analogs and derivatives beyond the scope of the aforementioned patents.

SUMMARY OF THE INVENTION

The present invention is directed to an analog or derivative of an alkyl fatty acid, such as but not limited to lipoic acid, having the general formula:

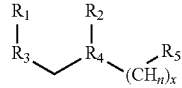

(1)

wherein n is 1-2 and x is 1-16, with the resulting hydrocarbon chain potentially being mixed saturated or unsaturated;

wherein $R_1$ and $R_2$ are independently hydrogen, alkyl, alkenyl, alkynyl, alkylaryl, heteroaryl, or alkylheteroaryl;

wherein $R_3$ and $R_4$ are independently a thioether, a thioester, an ether, an ester, an amine, an amide, a rare earth metal such as but not limited to gadolinium, a transition metal such as but not limited to platinum or indium, or a nonmetal such as but not limited to selenium;

wherein $R_5$ is hydrogen, nitrogen, alkyl, alkenyl, alkynyl, alkylaryl, heteroaryl, alkylheteroaryl, an ether, an amine, an amide, a phosphonium, a phosphonate, or a sulfonic acid;

and salts, prodrugs, or solvates thereof.

Specific examples are provided hereinbelow.

In a further embodiment of the present invention, a therapeutically-effective amount of at least one alkyl fatty acid analog or derivative as described herein is combined with at least one pharmaceutically-acceptable carrier or excipient therefor to form a pharmaceutical formulation useful for the treatment, prevention, imaging, or diagnosis of a disease of warm-blooded animals, including humans, wherein diseased cells or tissue are sensitive to such alkyl fatty acid analogs or derivatives. The at least one alkyl fatty acid analog or derivative is present in an amount from about 0.001 $mg/m^2$ to about 10 $g/m^2$. Additionally, as any or all of these analogs or derivatives may be metabolized within the diseased cell, or mitochondrion or other organelle thereof, it is expressly intended that metabolites of the above-referenced analogs or derivatives be within the scope of the present invention. Furthermore, in each of the general formulae, the (R)-isomer of each particular compound possesses greater physiological activity than does the (S)-isomer. Consequently, the at least one analog or derivative should be administered either solely in the (R)-isomer form or in a mixture of the (R)- and (S)-isomers.

In a still further embodiment of the present invention, there is provided a method of treating, preventing, imaging, or diagnosing a disease characterized by disease cells or tissue of warm-blooded animals, including humans, that are sensitive to administration of an alkyl fatty acid analog or derivative as described herein, comprising administering to a patient in need thereof a therapeutically-effective amount of at least one alkyl fatty acid analog or derivative according to any of the embodiments of the invention. In a preferred embodiment, the at least one alkyl fatty acid analog or derivative is combined with at least one pharmaceutically-acceptable carrier therefor to form a pharmaceutical formulation.

DETAILED DESCRIPTION OF THE INVENTION

The present invention is directed to novel analogs or derivatives of an alkyl fatty acid, such as but not limited to lipoic acid, having the general formula:

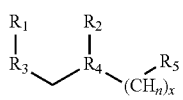

(1)

wherein n is 1-2 and x is 1-16, with the resulting hydrocarbon chain potentially being mixed saturated or unsaturated;

wherein $R_1$ and $R_2$ are independently hydrogen, alkyl, alkenyl, alkynyl, alkylaryl, heteroaryl, or alkylheteroaryl;

wherein $R_3$ and $R_4$ are independently a thioether, a thioester, an ether, an ester, an amine, an amide, a rare earth metal such as but not limited to gadolinium, a transition metal such as but not limited to platinum or indium, or a nonmetal such as but not limited to selenium;

wherein R₅ is alkyl, alkenyl, alkynyl, alkylaryl, heteroaryl, or alkylheteroaryl;

wherein R₆ is hydrogen, nitrogen, alkyl, alkenyl, alkynyl, alkylaryl, heteroaryl, alkylheteroaryl, an ether, an amine, an amide, a phosphonium, a phosphonate, or a sulfonic acid;

and salts, prodrugs, or solvates thereof.

Particular alkyl fatty acid analogs or derivatives according to general formula (1) include:

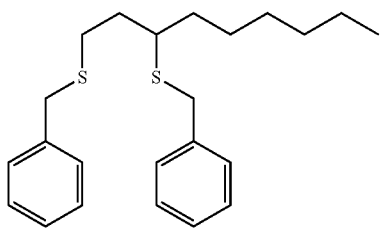
(A)

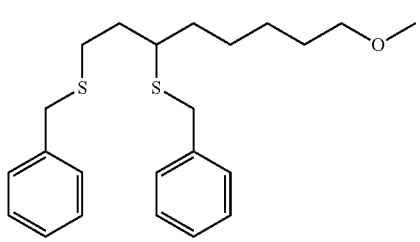
(B)

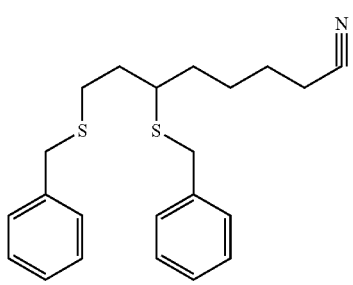
(C)

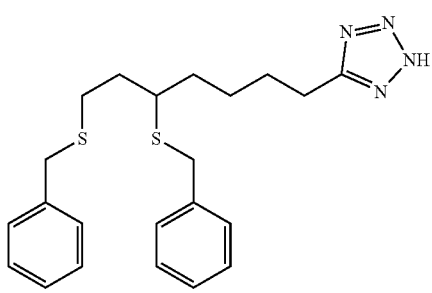
(D)

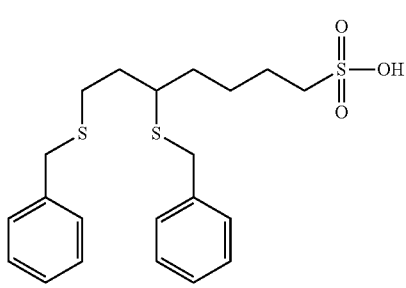
(E)

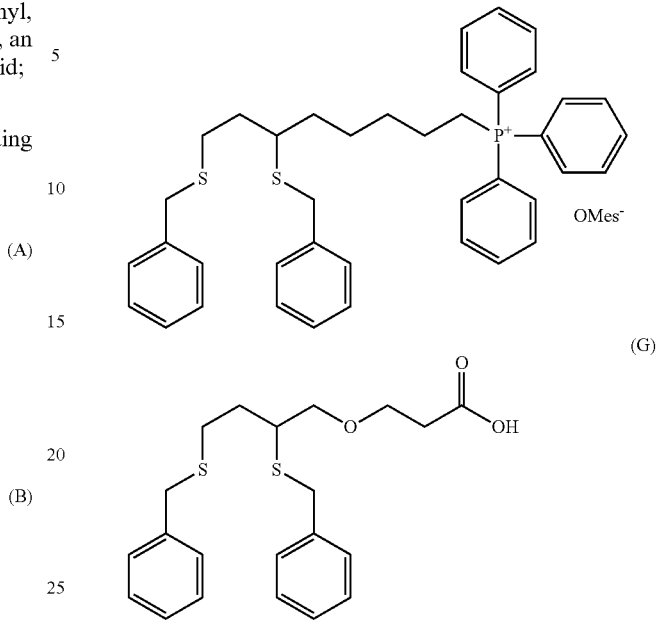
(F)

(G)

As used herein, alkyl is defined as $C_nH_{2n+1}$, wherein n is 1-16. Alkyl groups can be either aliphatic (straight or branched chain) or alicyclic; alicyclic groups may have additions or substitutions on any of the carbons to form heterocyclics. At least one heteroatom such as N, O or S may be present in a given alkyl group, i.e., in the carbon chain. Alkyl groups may be substituted or unsubstituted on any of their carbons.

As used herein, alkenyl is defined as $C_nH_{2n-1}$, wherein n is 1-16. Alkenyl groups can be either aliphatic (straight or branched chain) or alicyclic; alicyclic groups may have additions or substitutions on any of the carbons to form heterocyclics. At least one heteroatom such as N, O or S may be present in a given alkenyl group, i.e., in the carbon chain. Alkenyl groups may be substituted or unsubstituted on any of their carbons.

As used herein, alkynyl is defined as $C_mH_{2m-3}$, where m is 2-10. Alkynyl groups can be either aliphatic (straight or branched chain) or alicyclic; alicyclic groups may have additions or substitutions on any of the carbons to form heterocyclics. At least one heteroatom such as N, O or S may be present in a given alkynyl group, i.e., in the carbon chain. Alkynyl groups may be substituted or unsubstituted on any of their carbons.

As used herein, aryl refers to any univalent organic radical derived from an aromatic hydrocarbon by removing a hydrogen atom. Aryl is preferably an unsaturated ring system having 5-10 carbon atoms. Aryl also includes organometallic aryl groups such as ferrocene. Aryl groups may be substituted or unsubstituted on any of their carbons.

As used herein, heteroaryl refers to an aromatic heterocyclic ring system (monocyclic or bicyclic) where the heteroaryl moieties are five- or six-membered rings containing 1-4 heteroatoms selected from the group consisting of S, N, and O. Heteroaryl groups may be substituted or unsubstituted on any of their atoms especially on the carbon atoms.

As used herein, acyl is defined as RC(O)—, where R can be, without limitation, hydrogen, alkyl, alkenyl, alkynyl, cycloalkyl, aryl, alkylaryl, heteroaryl, or heterocyclyl, any of which can be substituted or unsubstituted.

Exemplary substituents for the above-described groups include, without limitation, alkyl, alkenyl, alkynyl, aryl, heteroaryl, acyl, alkoxycarbonyl, alkoxy, alkoxyalkyl, alkoxyalkoxy, cyano, halogen, hydroxy, nitro, oxo, trifluoromethyl, trifluoromethoxy, trifluoropropyl, amino, amido, alkylamino, dialkylamino, dialkylaminoalkyl, hydroxyalkyl, alkoxyalkyl, alkylthio, —SO$_3$H, —SO$_2$NH$_2$, —SO$_2$NH(alkyl), —SO$_2$N(alkyl)$_2$, —CO$_2$H, CO$_2$NH$_2$, CO$_2$NH(alkyl), and —CO$_2$N(alkyl)$_2$. In addition, any number of substitutions may be made on any of the above-described groups; in other words, it is possible to have a mono-, di-, tri-, etc. substituted group, and the substituents themselves may also be substituted. Further, any of the groups may be appropriately generally substituted with any of a carbohydrate, a lipid, a nucleic acid, an amino acid, or a polymer of any of those, or a single or branched chain synthetic polymer (having a molecular weight ranging from about 350 to about 40,000).

Amines may be primary, secondary, or tertiary.

Thioester or thioether linkages can be oxidized to produce sulfoxides or sulfones; in other words, the —S— in the linkage could be —S(O)— or —S(O)$_2$. In addition, thioester or thioether linkages may further comprise disulfides that can be oxidized to thiosulfinic or thiosulfonic acids; in other words, instead of —S— in a linkage, the linkage could be —S(O)—S— or —S(O)$_2$—S—.

A therapeutically-effective amount of at least one alkyl fatty acid analog or derivative of any one of the aforementioned embodiments may be administered to a subject for the treatment, prevention, diagnosis, and/or imaging of a disease, or symptoms thereof, in warm-blooded animals. Alternatively, in another embodiment of the present invention, a therapeutically-effective amount of at least one alkyl fatty acid analogs or derivative of any one of the aforementioned embodiments is combined with at least one pharmaceutically-acceptable carrier or excipient therefor to form a pharmaceutical formulation useful for the treatment, prevention, diagnosis, and/or imaging of a disease, or symptoms thereof, in warm-blooded animals. Such animals include those of the mammalian class, such as humans, horses, cattle, domestic animals including dogs and cats, and the like. Examples of pharmaceutically-acceptable carriers are well known in the art and include those conventionally used in pharmaceutical compositions, such as, but not limited to, solvents, diluents, surfactants, solubilizers, salts, antioxidants, buffers, chelating agents, flavorants, colorants, preservatives, absorption promoters to enhance bioavailability, antimicrobial agents, and combinations thereof, optionally in combination with other therapeutic ingredients. When used in medicine, the salts should be pharmaceutically acceptable, but non-pharmaceutically-acceptable salts may conveniently be used to prepare pharmaceutically-acceptable salts thereof and are not excluded from the scope of the invention. Such pharmacologically- and pharmaceutically-acceptable salts include, but are not limited to, those prepared from the following acids: hydrochloric, hydrobromic, sulfuric, nitric, phosphoric, maleic, acetic, palicylic, p-toluene sulfonic, tartaric, citric, methane sulfonic, formic, malonic, succinic, naphthalene-2-sulfonic, and benzene sulfonic. Also, pharmaceutically-acceptable salts can be prepared as alkaline metal or alkaline earth salts, such as sodium, potassium or calcium salts of the carboxylic acid group.

Solvents particularly suitable for use herein include benzyl alcohol, dimethylamine, isopropyl alcohol and combinations thereof; one of ordinary skill in the art would readily recognize that it may be desirable to first dissolve the at least one lipoic acid derivative in a suitable solvent and then to dilute the solution with a diluent.

When a pharmaceutical formulation suitable for intravenous administration is desired, a suitable diluent would be employed. Any conventional aqueous or polar aprotic solvent is suitable for use in the present invention. Suitable pharmaceutically acceptable diluents include, without limitation, saline, a sugar solution, alcohols such as ethyl alcohol, methanol and isopropyl alcohol, polar aprotic solvents such as dimethylformamide (DMF), dimethylsulfoxide (DMSO) and dimethylacetamide (DMA), and combinations thereof. A preferred pharmaceutically acceptable diluent is a dextrose solution, more preferably a dextrose solution containing from about 2.5% to about 10%, more preferably about 5%, dextrose by weight. The pharmaceutically acceptable diluent is typically employed in a non-homolysis generating amount; one of ordinary skill in the art can readily determine an amount of diluent suitable for use in a pharmaceutical formulation according to the present invention.

As used herein, a therapeutically-effective amount refers to the dosage or multiple dosages of the alkyl fatty acid analog or derivative at which the desired effect is achieved. Generally, an effective amount of the analog or derivative may vary with the activity of the specific agent employed; the metabolic stability and length of action of that agent; the species, age, body weight, general health, dietary status, sex and diet of the subject; the mode and time of administration; rate of excretion; drug combination, if any; and extent of presentation and/or severity of the particular condition being treated. The precise dosage can be determined by an artisan of ordinary skill in the art without undue experimentation, in one or several administrations per day, to yield the desired results, and the dosage may be adjusted by the individual practitioner to achieve a desired effect or in the event of any complication.

The alkyl fatty acid analog or derivative of the present invention can be delivered, by any means, in any amount desired up to the maximum amount that can be administered safely to a patient. The amount of the analog or derivative may range from less than 0.01 mg/mL to greater than 1000 mg/mL, preferably about 50 mg/mL.

Generally, the alkyl fatty acid analog or derivative of the present invention will be delivered in a manner sufficient to administer to the patient an amount effective to deliver the agent to its intended molecular target. The dosage amount may thus range from about 0.001 mg/m$^2$ to about 10 g/m$^2$, preferably about 60 mg/m$^2$. The dosage amount may be administered in a single dose or in the form of individual divided doses, such as from one to four or more times per day. In the event that the response in a subject is insufficient at a certain dose, even higher doses (or effective higher doses by a different, more localized delivery route) may be employed to the extent of patient tolerance.

As any or all of these analogs or derivatives may be metabolized within the diseased cell, or mitochondrion or other organelle thereof, upon administration to the patient, it is expressly intended that metabolites of the above-referenced analogs or derivatives be within the scope of the present invention. Furthermore, in each of the general formulae, the (R)-isomer of each particular compound possesses greater physiological activity than does the (S)-isomer.

Consequently, the at least one analog or derivative should be administered either solely in the (R)-isomer form or in a mixture of the (R)- and (S)-isomers.

The pharmaceutical formulation of the present invention can be prepared according to conventional formulation techniques and may take any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, emulsions, nanoemulsions, aerosols, sprays, gels, lotions, creams, ointments, and the like. If such a formulation is desired, other additives well-known in the art may be included to impart the desired consistency and other properties to the formulation. For example, a stock solution of the at least one alkyl fatty acid analog or derivative can be prepared according to conventional techniques and then diluted as desired by a pharmaceutically-acceptable diluent to form a liquid preparation such as a sterile parenteral solution.

The pharmaceutical formulation of the present invention may be administered using any mode of administration both that is medically acceptable and that produces effective levels of the agent without causing clinically-unacceptable adverse effects. Although formulations specifically suited for parenteral administration are preferred, the pharmaceutical formulation of the present invention may be contained in any suitable vessel, such as a vial or ampoule, and suitable for via one of several routes including inhalational, oral, topical, transdermal, nasal, ocular, pulmonary, rectal, transmucosal, intravenous, intramuscular, intradermal, subcutaneous, intraperitoneal, intrathoracic, intrapleural, intrauterine, intratumoral, or infusion methodologies or administration, without limitation. Those skilled in the art will recognize that the mode of administering the analog or derivative of the present invention depends on the type of disease or symptom to be treated. Likewise, those skilled in the art will also recognize that particular pharmaceutically-acceptable carriers or excipients will vary from pharmaceutical formulations suitable for one administration mode to those suitable for another administration mode.

In a further embodiment of the present invention, there is provided a method of treating, preventing, imaging, and/or diagnosing a disease characterized by diseased cells or tissue that are sensitive to alkyl fatty acid analogs or derivatives according to the present invention, comprising administering to a patient in need thereof a therapeutically-effective amount of at least one such analog or derivative. In a preferred embodiment, the at least one alkyl fatty acid analog or derivative is incorporated into a pharmaceutical formulation according to the present invention.

The alkyl fatty acid analogs or derivatives of the present invention, and pharmaceutical formulations thereof, may be used to treat, prevent, image, or diagnose diseases involving altered or distinct cellular PDH, α-KDH, ADH, and/or BCKADH complex activity. Cells with altered or deranged PDH, α-KDH, ADH, and/or BCKADH complex activity are particularly targeted, so that upon administration, the analog or derivative of the present invention is selectively and specifically delivered to and taken up by a tumor mass and the transformed cells within, and effectively concentrated within the mitochondria of those cells, thereby sparing healthy cells and tissue from the effects of the analog or derivative. Hence, the agent of the present invention is particularly suited for treatment for diseases characterized by cellular hyperproliferation. The skilled artisan can readily identify diseases presenting such activity or alternatively can readily screen the disease of interest for sensitivity to such analogs or derivatives.

The alkyl fatty acid analogs or derivatives of the present invention, and pharmaceutical formulations thereof, are expected to be useful in such general cancer types as carcinoma, sarcoma, lymphoma and leukemia, germ cell tumor, and blastoma. More specifically, the pharmaceutical composition of the present invention is expected to be useful in primary or metastatic melanoma, lung cancer, liver cancer, Hodgkin's and non-Hodgkin's lymphoma, uterine cancer, cervical cancer, bladder cancer, kidney cancer, colon cancer, and adenocarcinomas such as breast cancer, prostate cancer, ovarian cancer, and pancreatic cancer, without limitation. Non-limiting examples of other diseases characterized by cellular hyperproliferation amenable to the agent of the present invention include age-related macular degeneration; Crohn's disease; cirrhosis; chronic inflammatory-related disorders; diabetic retinopathy or neuropathy; granulomatosis; immune hyperproliferation associated with organ or tissue transplantation; an immunoproliferative disease or disorder (e.g., inflammatory bowel disease, psoriasis, rheumatoid arthritis, or systemic lupus erythematosus); vascular hyperproliferation secondary to retinal hypoxia; or vasculitis.

By adapting the methods described herein, the alkyl fatty acid analogs or derivatives of the present invention, and pharmaceutical formulations thereof, may also be used in the treatment, prevention, imaging, or diagnosis of diseases other than those characterized by cellular hyperproliferation. For example, eukaryotic pathogens of humans and other animals are generally much more difficult to treat than bacterial pathogens because eukaryotic cells are so much more similar to animal cells than are bacterial cells. Such eukaryotic pathogens include protozoans such as those causing malaria as well as fungal and algal pathogens. Because of the remarkable lack of toxicity of the alkyl fatty acid analogs or derivatives of the present invention to non-transformed human and animal cells, and because many eukaryotic pathogens are likely to pass through life cycle stages in which their PDH, α-KDH, ADH, and/or BCKADH complexes become sensitive to such analogs or derivatives, the alkyl fatty acid analogs or derivatives of the present invention, and pharmaceutical formulations thereof, can be used as bacteriocidal agents.

Specific embodiments of the invention will now be demonstrated by reference to the following examples. It should be understood that these examples are disclosed solely by way of illustrating the invention and should not be taken in any way to limit the scope of the present invention.

EXAMPLE 1

Screening of Analogs for Cell Kill Activity in Cancer Cells

Objective

The objective of this investigation was to assess the in vitro cell killing activities of analogs of lipoic acid in BXPC3 human pancreatic, H460 non small lung carcinoma, and SF539 human gliosarcoma cancer cells.

Materials and Methods

Materials

All materials were obtained through normal distribution channels from the manufacturer stated.

Costar opaque-walled plate, Corning Costar Corporation, Cambridge, Mass., cat. no. 3917, Fisher Scientific cat no. 07-200-628

FLUOstar OPTIMA, BMG LABTECH, Offenburg, Germany

CellTiter Glo® (CTG) Luminescent Cell Viability Assay, Promega, Fisher Scientific cat no. PR-G7573

RPMI 1640 Tissue culture medium, Mediatech, Fisher Scientific cat. no. MT-10040-CV Fetal Bovine Serum (FBS), Fisher Scientific cat. no. MTT35011CV Penicillin and Steptomycin, Fisher Scientific cat. no. MT 30-009-CI Tumor Cell Lines Three human tumor cell types, BXPC3 human pancreatic cancer, H460 non small lung carcinoma, and SF539 human gliosarcoma, were used in this investigation. The BXPC3 and H460 cells were originally obtained from American Type Cell Culture (ATCC). The SF539 cells were originally obtained from the NCI AIDS and Cancer Specimen Bank (ACSB). All tumor cells were maintained at 37° C. in a humidified 5% $CO_2$ atmosphere in T75 tissue culture flasks containing 20 mL of Roswell Park Memorial Institute (RPMI) 1640 containing 2 mM L-glutamine, 10% FBS and 1% penicillin and streptomycin (100 IU/mL penicillin and 100 µg/mL streptomycin). The tumor cells were split at a ratio of 1:5 every 4-5 days by trypsinization and resuspended in fresh medium in a new flask. Cells were harvested for experiments at 70-90% confluency.

Test Articles

Stock solutions of each analog were prepared at a concentration of 200 and 100 mM in DMSO. Five µL of this solution was diluted in 10.0 mL of 0.5% serum containing RPMI media to give the desired 100 µM and 50 µM solutions in 0.05% DMSO.

Study Procedures

Study Design

The cancer cells were seeded at 4000 cells/well for H460 cells and 6000 cells/well for BXPC3 and SF 539 cells and incubated 24 hours. The killing activity of analogs was assayed at 50 µM and 100 µM concentrations. The tumor cells were treated for 24 hours with the test article, and after 24 hours of treatment the number of viable tumor cells was determined using the CTG assay.

Cell Seeding for Experiments

Cells were grown to 70-90% confluency, medium was removed, and the cell monolayers were washed briefly by adding 5 mL of phosphate buffer saline (PBS) followed by aspiration. Trypsin-ethylenediaminetetraacetic acid (EDTA) (4 mL) was added to each flask, and the flask was placed in the tissue culture incubator for 5 minutes. Serum-containing medium (10 mL) was added to halt the enzymatic reactions, and cells were disaggregated by repeated resuspension with serological pipette. The cell-containing medium (20 µL) was added to 20 µL of 0.4% Trypan Blue solution, mixed, and 10 µL of this cell-containing mixture was placed in a chamber of the hemocytometer. The number of viable cells was determined by counting the number of viable cells (cells that excluded Trypan Blue) in the four corner squares of the hemocytometer chamber at 100× magnification, to get the average number of cells present. The volume of cells needed was determined by the following formula:

$$\text{Volume of cells needed} = \frac{\text{\# of cells need for the assay (mL)}}{\text{\# of cells counted (mL)}}$$

where # of cells counted (mL)=average # of cells on hemocytometer×2 (dilution factor)×$10^4$.

The number of cells targeted for the study is $4 \times 10^3$ per well for H460 cells and $6 \times 10^3$ per well for BXPC3 and SF539 cells in 100 µL of medium. The actual number of cells were counted and seeded in the wells of a 96 well-plate. The cells were incubated for approximately 24 hours before addition of test article.

Treatment with Test Article

The media in the plate was removed by aspiration, and 100 µL of the test article at a final concentration of 50 µM or 100 µM was added to the cells. After exposure to the test articles for 24 hours, the number of viable cells in each well was determined and the percent of viable cells relative to control (in the absence of test article) were calculated. Additionally, a set of wells was treated with cell culture medium in the absence of cells to obtain a value for background luminescence. A separate set of cells was seeded at the same time in a clear 96-well plate and observed under the microscope at 24 hours, following addition of the test article to estimate the amount of cells present after treatment.

Determination of the Number of Viable Cells by the CTG Assay

The number of viable cells was determined by using the CTG assay. Specifically, reagents were mixed and allowed to come to room temperature according to instructions from Promega, Inc. (Madison, Wis.). Cell plates were removed from the cell culture incubator and left on the bench for thirty minutes until they reached room temperature. 100 µL per well of CTG reagent was added with the 12-channel Eppendorf pipettor. The cells were lysed by shaking the plate for two minutes in a shaker. The cells were kept in room temperature for ten minutes to stabilize the luminescent signal. The luminescence was measured using the FLUOstar OPTIMA plate reader (BMG Labtech, Inc., Durham, N.C.).

Calculation of Cell Killing Activity

Data from luminescence readings was copied onto EXCEL spreadsheets, and cell growth relative to untreated cells was calculated, using the following equation:

$$\% \text{ growth related to } NT = \frac{\text{mean luminescence of the test article}}{\text{mean luminescence untreated}} \times 100\%$$

RESULTS AND CONCLUSION

The results of the experiment are summarized in Table 1.

TABLE 1

Comparison of in vitro cancer cell killing activity of analogs of the present invention % Viable Cells Remaining (0.5% serum and 0.05% DMSO)

| Article | BXPC3 | | H460 | | SF539 | |
|---|---|---|---|---|---|---|
| | % avg live cells @ 50 μM | % avg live cells @ 100 μM | % avg live cells @ 50 μM | % avg live cells @ 100 μM | % avg live cells @ 50 μM | % avg live cells @ 100 μM |
| A | 84.0 | 75.0 | 89.0 | 70.0 | 100.0 | 98.0 |
| B | 84.0 | 91.0 | 97.0 | 67.0 | 99.0 | 99.0 |
| C | 70.9 | 36.1 | 69.8 | 27.1 | 74.9 | 23.2 |
| D | 0.3 | 3.9 | 4.1 | 2.7 | 2.1 | 0.1 |
| E | 0.0 | 0.0 | 0.0 | 0.3 | 0.0 | 0.0 |
| F | 2.0 | 3.9 | 2.4 | 4.0 | 0.0 | 0.0 |
| G | 99.7 | 41.7 | 101.7 | 37.6 | 91.6 | 30.3 |

As is evident from Table 1, each of the analogs of the present invention demonstrated in vitro cell killing activity against at least one of the cancer cell lines tested at either the 50 μM concentration, the 100 μM concentration, or both.

The foregoing discussion discloses and describes merely exemplary embodiments of the present invention. One skilled in the art will readily recognize from such discussion, and from the accompanying claims, that various changes, modifications and variations can be made therein without departing from the spirit and scope of the invention as defined in the following claims. Furthermore, while exemplary embodiments have been expressed herein, others practiced in the art may be aware of other designs or uses of the present invention. Thus, while the present invention has been described in connection with exemplary embodiments thereof, it will be understood that many modifications in both design and use will be apparent to those of ordinary skill in the art, and this application is intended to cover any adaptations or variations thereof. It is therefore manifestly intended that this invention be limited only by the claims and the equivalents thereof. Additionally, all patent applications, patents, and other publications cited herein are incorporated by reference in their entirety.

The invention to be claimed is:

1. An alkyl fatty acid analog having the general formula:

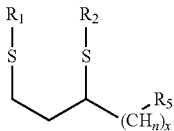

wherein:
n is 2;
x is 1-16;
$R_1$ and $R_2$ are independently alkylaryl or alkylheteroaryl; and
$R_5$ is heteroaryl attached to the $(CH_n)_x$ via a carbon atom of the heteroaryl group;
or a salt thereof.

2. The analog of claim 1, wherein $R_1$ and $R_2$ are independently alkylaryl.

3. The analog of claim 1, wherein $R_1$ and $R_2$ are independently alkylheteroaryl.

4. The analog of claim 1, wherein the heteroaryl is a 5-membered or 6-membered monocyclic aromatic ring containing 1-4 heteroatoms selected from the group consisting of S, N, and O.

5. The analog of claim 2, wherein the heteroaryl is a 5-membered or 6-membered monocyclic aromatic ring containing 1-4 heteroatoms selected from the group consisting of S, N, and O.

6. The analog of claim 1, wherein the heteroaryl is unsubstituted.

7. The analog of claim 4, wherein the heteroaryl is unsubstituted.

8. The analog of claim 5, wherein the heteroaryl is unsubstituted.

9. The analog of claim 1, wherein the heteroaryl is substituted by one or more substituents independently selected from the group consisting of alkyl, alkenyl, alkynyl, acyl, alkoxycarbonyl, alkoxy, alkoxyalkyl, alkoxyalkoxy, cyano, halogen, hydroxy, nitro, trifluoromethyl, trifluoromethoxy, trifluoropropyl, amino, amido, alkylamino, dialkylamino, dialkylaminoalkyl, hydroxyalkyl, alkoxyalkyl, alkylthio, —$SO_3H$, —$SO_2NH_2$, —$SO_2NH(alkyl)$, —$SO_2N(alkyl)_2$, —$CO_2H$, —$CO_2NH_2$, —$CO_2NH(alkyl)$, and —$CO_2N(alkyl)_2$.

10. The analog of claim 4, wherein the heteroaryl is substituted by one or more substituents independently selected from the group consisting of alkyl, alkenyl, alkynyl, acyl, alkoxycarbonyl, alkoxy, alkoxyalkyl, alkoxyalkoxy, cyano, halogen, hydroxy, nitro, trifluoromethyl, trifluoromethoxy, trifluoropropyl, amino, amido, alkylamino, dialkylamino, dialkylaminoalkyl, hydroxyalkyl, alkoxyalkyl, alkylthio, —$SO_3H$, —$SO_2NH_2$, —$SO_2NH(alkyl)$, —$SO_2N(alkyl)_2$, —$CO_2H$, —$CO_2NH_2$, —$CO_2NH(alkyl)$, and —$CO_2N(alkyl)_2$.

11. The analog of claim 5, wherein the heteroaryl is substituted by one or more substituents independently selected from the group consisting of alkyl, alkenyl, alkynyl, acyl, alkoxycarbonyl, alkoxy, alkoxyalkyl, alkoxyalkoxy, cyano, halogen, hydroxy, nitro, trifluoromethyl, trifluoromethoxy, trifluoropropyl, amino, amido, alkylamino, dialkylamino, dialkylaminoalkyl, hydroxyalkyl, alkoxyalkyl, alkylthio, —$SO_3H$, —$SO_2NH_2$, —$SO_2NH(alkyl)$, —$SO_2N(alkyl)_2$, —$CO_2H$, —$CO_2NH_2$, —$CO_2NH(alkyl)$, and —$CO_2N(alkyl)_2$.

12. A pharmaceutical formulation comprising at least one alkyl fatty acid analog of claim 1 and at least one pharmaceutically acceptable carrier.

13. A pharmaceutical formulation comprising at least one alkyl fatty acid analog of claim 4 and at least one pharmaceutically acceptable carrier.

14. A pharmaceutical formulation comprising at least one alkyl fatty acid analog of claim 5 and at least one pharmaceutically acceptable carrier.

15. A method of treating a disease selected from primary melanoma, metastatic melanoma, lung cancer, liver cancer, Hodgkin's lymphoma, non-Hodgkin's lymphoma, uterine cancer, cervical cancer, bladder cancer, kidney cancer, colon cancer, breast cancer, prostate cancer, ovarian cancer, pancreatic cancer, and a sarcoma, comprising administering to a patient in need thereof a therapeutically effective amount of at least one alkyl fatty acid analog according to claim 1 to treat the disease.

16. The method of claim 15, wherein the disease is lung cancer, pancreatic cancer, or a sarcoma.

17. The method of claim 15, wherein the at least one alkyl fatty acid analog is the analog according to claim 4.

18. The method of claim 15, wherein the at least one alkyl fatty acid analog is the analog according to claim 5.

* * * * *